(12) United States Patent
Matsumoto et al.

(10) Patent No.: US 6,458,988 B1
(45) Date of Patent: Oct. 1, 2002

(54) PRODUCTION PROCESS FOR HYDROXYALKYL(METH)ACRYLATE

(75) Inventors: Hajime Matsumoto, Himeji (JP); Tokumasa Ishida, Himeji (JP); Yasuhiro Shingai, Himeji (JP); Masatoshi Ueoka, Himeji (JP); Yukihiro Yoneda, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 228 days.

(21) Appl. No.: 09/664,953

(22) Filed: Sep. 16, 2000

(30) Foreign Application Priority Data

| Oct. 6, 1999 | (JP) | 11-285887 |
| Oct. 6, 1999 | (JP) | 11-285888 |
| Jan. 31, 2000 | (JP) | 2000-022692 |
| Feb. 9, 2000 | (JP) | 2000-032340 |

(51) Int. Cl.$^7$ .................. C07C 67/26; C07C 69/52; C07C 69/00
(52) U.S. Cl. .................. 560/209; 560/205; 560/129
(58) Field of Search ................. 560/209, 205, 560/129

(56) References Cited

U.S. PATENT DOCUMENTS

| 3,340,295 A | 9/1967 | Wheeler et al. |
| 3,804,884 A | 4/1974 | Jeffrey et al. |

FOREIGN PATENT DOCUMENTS

| EP | 1090903 A2 | * 11/2001 |
| JP | 41-13019 | 7/1966 |
| JP | 43-18890 B | 8/1968 |
| JP | 61-27945 A | 2/1986 |
| JP | 64-6182 B2 | 2/1989 |
| JP | 6-720 B2 | 1/1994 |
| JP | B-6-720 | * 1/1994 |
| JP | 10-237021 A | 9/1998 |
| JP | 10-330320 A | 12/1998 |
| JP | 11240853 | * 9/1999 |
| JP | 11-240853 A | 9/1999 |

* cited by examiner

Primary Examiner—Alan L. Rotman
Assistant Examiner—Hector Reyes
(74) Attorney, Agent, or Firm—Haugen Law Firm PLLP

(57) ABSTRACT

A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, wherein: (1) the stripping step is performed by use of an inert gas, and the concentration of oxygen in the inert gas is adjusted in the range of 0.1 to 5 mol %; (2) the concentration of the unreacted residue of the (meth)acrylic acid in the resultant reaction liquid is suppressed to not higher than 10 weight %; (3) the difference in operational pressure between the stripping step and the absorption step of causing a solvent to absorb the stripped alkylene oxide is suppressed to not more than 1,000 hPa; (4) the reaction liquid resultant from the reaction is directly supplied to the stripping step without being heated; (5) a part of the liquid left behind in the stripping step is heated and then supplied to the stripping step again; (6) a hydroxyalkyl (meth)acrylate solution is used as the absorbing solvent; (7) a part of the liquid resultant from the absorption step is cooled and then supplied to the absorption step again; or (8) a part or the whole of the absorbing liquid which is on the way of the absorption step is extracted and then cooled and then supplied to the absorption step again.

12 Claims, 5 Drawing Sheets

US 6,458,988 B1

PRODUCTION PROCESS FOR HYDROXYALKYL(METH)ACRYLATE

BACKGROUND OF THE INVENTION

A. Technical Field

The present invention relates to a production process for a hydroxyalkyl(meth)acrylate, which comprises the step of carrying out a reaction between (meth)acrylic acid and an alkylene oxide.

B. Background Art

As to production processes for a hydroxyalkyl(meth) acrylate which comprises the step of carrying out a reaction between (meth)acrylic acid and an alkylene oxide, it is known that the alkylene oxide is supplied to a reactor in a molar quantity excessive to (meth)acrylic acid so that the formation of by-products can be inhibited, and that the conversion can be enhanced as much as possible (e.g. JP-B-013019/1966, JP-B-018890/1968). In this case, the unreacted residue of the alkylene oxide is present in the resultant reaction liquid at the end of the reaction. Therefore, after being separated from the reaction liquid, this residue needs to be disposed of, or recovered and recycled.

In the case where the unreacted residue of the alkylene oxide is stripped by vaporization under reduced pressure in order to separate it from the reaction liquid, the stripping efficiency would be bad without the reaction liquid being put under high vacuum, because the alkylene oxide much dissolves into the reaction liquid. Therefore, a high cost is needed for vacuum facilities which are used to achieve high vacuum. In addition, under reduced pressure, the reaction liquid undergoes asphyxiation polymerization because oxygen dissolved in the reaction liquid is deaerated.

On the other hand, the recovering and recycling is economically advantageous. However, in the case where the unreacted residue of the alkylene oxide is stripped by vaporization under reduced pressure, a refrigerant having an extremely low temperature is necessary for the condensation of the vaporized alkylene oxide gas by use of the refrigerant under reduced pressure, therefore the resultant process cost is high.

Thus, if the alkylene oxide gas as vaporized under reduced pressure is condensed by compression to not lower than normal pressure with a compressor, then the temperature of the refrigerant can be set to be high. However, when the alkylene oxide gas is adiabatically compressed, the gas temperature rises to enlarge a danger of explosion.

In addition, JP-A-330320/1998 discloses that the unreacted alkylene oxide residue can be effectively utilized by causing it to be absorbed into raw (meth)acrylic acid and then recycling this (meth)acrylic acid containing the ethylene oxide for the addition reaction. However, in respect to the recovery efficiency, this prior art cannot be said to be on a sufficiently satisfactory level.

SUMMARY OF THE INVENTION

A. Object of the Invention

An object of the present invention is to provide a production process for a hydroxyalkyl(meth)acrylate which comprises the steps of carrying out a reaction between (meth)acrylic acid and an alkylene oxide and stripping the unreacted residue of the alkylene oxide from the resultant reaction liquid, wherein the production process enables to safely and efficiently strip the unreacted residue of the alkylene oxide, or enables to economically and efficiently recover and recycle the unreacted residue of the alkylene oxide.

B. Disclosure of the Invention

The present inventors diligently studied to solve the above-mentioned problems. As a result, the inventors hit on an idea that: if (1) an inert gas having a specific composition is used as a stripping means, then there is no danger of explosion, and the possibility of the asphyxiation polymerization in a stripping apparatus can be lessened. Furthermore, the inventors found that: also if (2) the concentration of the unreacted residue of the (meth)acrylic acid in the resultant reaction liquid is suppressed to not more than a specific value, then the effects of the present invention are sufficiently exhibited.

In addition, the inventors further hit on an idea that: in the case where the production process further comprises the step of causing the unreacted residue of the alkylene oxide to be absorbed after the step of stripping the unreacted residue of the alkylene oxide from the resultant reaction liquid, if (3) the difference in operational pressure between the steps of stripping the unreacted residue of the alkylene oxide from the resultant reaction liquid and causing the stripped alkylene oxide to be absorbed is suppressed to not more than a specific value, then both the stripping efficiency and the absorption efficiency can be maintained on a practical use level, while the danger of explosion of the unreacted alkylene oxide residue can be avoided.

In addition, it is generally preferable, for enhancing the stripping efficiency, that the temperature of the reaction liquid is high when the reaction liquid is introduced into the stripping step. However, for example, in the case where the reaction liquid containing the unreacted residue of the alkylene oxide is subjected to a heating operation before being introduced into the stripping step, there are disadvantages in that there is a great danger of explosion. Thus, the inventors studied to seek a process that can enhance the stripping efficiency even if the reaction liquid is not heated before the stripping step. As a result, the inventors hit on the following two ideas.

Namely, the inventors hit on an idea that: if (4) the reaction liquid resultant from the reaction is directly supplied to the stripping step without being heated, then the stripping efficiency is enhanced due to sensible heat of the reaction liquid, and further, there is no danger of explosion. In addition, the inventors further hit on an idea that: if (5) a part of the liquid left behind in the stripping step is heated and then supplied to the stripping step again, the stripping temperature in the stripping step can be raised without raising the temperature of the reaction liquid as introduced into the stripping step, so the stripping efficiency can be enhanced without a danger of explosion.

Furthermore, the inventors directed their attention to a fact that, in the case of the mode further comprising the absorption step after the stripping step, the lower the temperature of the absorbing solvent becomes, the higher the absorption efficiency of the alkylene oxide becomes, and then the inventors considered that: (A) the lower the solidifying point of the absorbing solvent is, the more the cooling temperature can be lowered; and (B) the temperature of the solvent rises due to absorption of alkylene oxide vapor, therefore if the temperature rise of the solvent involved by this absorption can be suppressed the absorption efficiency is also enhanced. Then, from the above point (A), the inventors found that: if (6) a hydroxyalkyl(meth)acrylate of which the solidifying point (about −70° C.) is much lower than that (about 15° C.) of (meth)acrylic acid is used as the absorbing solvent, then the absorbing solvent can be cooled to a fairly low temperature, and further, the alkylene oxide can be recovered and recycled with a high efficiency. In addition, from the above point (B), the inventors found that: if (7) a part of the liquid resultant from the absorption step is cooled and then supplied to the absorption step again, or if (8) a part or the whole of the absorbing liquid which is on the way of the absorption step is extracted and then cooled and then supplied to the absorption step again, the temperature rise of the absorbing solvent can efficiently be suppressed.

The present invention has been completed in the above way.

That is to say, a production process for a hydroxyalkyl (meth)acrylate, according to the present invention, comprises the steps of carrying out a reaction between (meth) acrylic acid and an alkylene oxide and stripping the unreacted residue of the alkylene oxide from the resultant reaction liquid, with the production process being characterized in that the stripping step is performed by use of an inert gas, and in that the concentration of oxygen in the inert gas is adjusted in the range of 0.1 to 5 mol %.

Another production process for a hydroxyalkyl(meth) acrylate, according to the present invention, comprises the steps of carrying out a reaction between (meth)acrylic acid and an alkylene oxide and stripping the unreacted residue of the alkylene oxide from the resultant reaction liquid, with the production process being characterized in that the concentration of the unreacted residue of the (meth)acrylic acid in the resultant reaction liquid is suppressed to not higher than 10 weight %.

Yet another production process for a hydroxyalkyl(meth) acrylate, according to the present invention, comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that the difference in operational pressure between the stripping step and the absorption step is not more than 1,000 hPa.

Yet another production process for a hydroxyalkyl(meth) acrylate, according to the present invention, comprises the steps of carrying out a reaction between (meth)acrylic acid and an alkylene oxide and stripping the unreacted residue of the alkylene oxide from the resultant reaction liquid, with the production process being characterized in that the reaction liquid resultant from the reaction is directly supplied to the stripping step without being heated.

Yet another production process for a hydroxyalkyl(meth) acrylate, according to the present invention, comprises the steps of carrying out a reaction between (meth)acrylic acid and an alkylene oxide and stripping the unreacted residue of the alkylene oxide from the resultant reaction liquid, with the production process being characterized in that a part of the liquid left behind in the stripping step is heated and then supplied to the stripping step again.

Yet another production process for a hydroxyalkyl(meth) acrylate, according to the present invention, comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a hydroxyalkyl(meth)acrylate solution is used as the absorbing solvent.

Yet another production process for a hydroxyalkyl(meth) acrylate, according to the present invention, comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a part of the liquid resultant from the absorption step is cooled and then supplied to the absorption step again.

Yet another production process for a hydroxyalkyl(meth) acrylate, according to the present invention, comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a part or the whole of the absorbing liquid which is on the way of the absorption step is extracted and then cooled and then supplied to the absorption step again.

These and other objects and the advantages of the present invention will be more fully apparent from the following detailed disclosure.

EXPLANATION OF THE SYMBOLS

Figure 1:
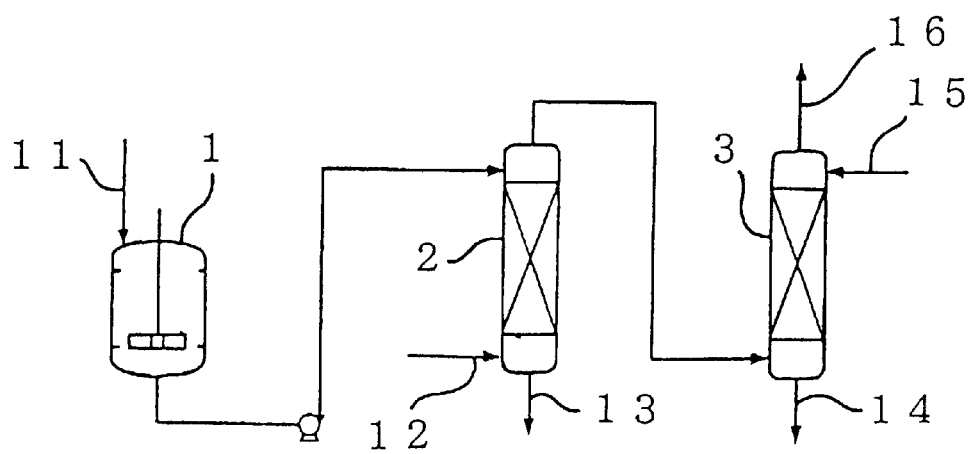
FIG. 1 is a flow chart which illustrates an example of production processes utilizing the production process according to the present invention.
Figure 2:
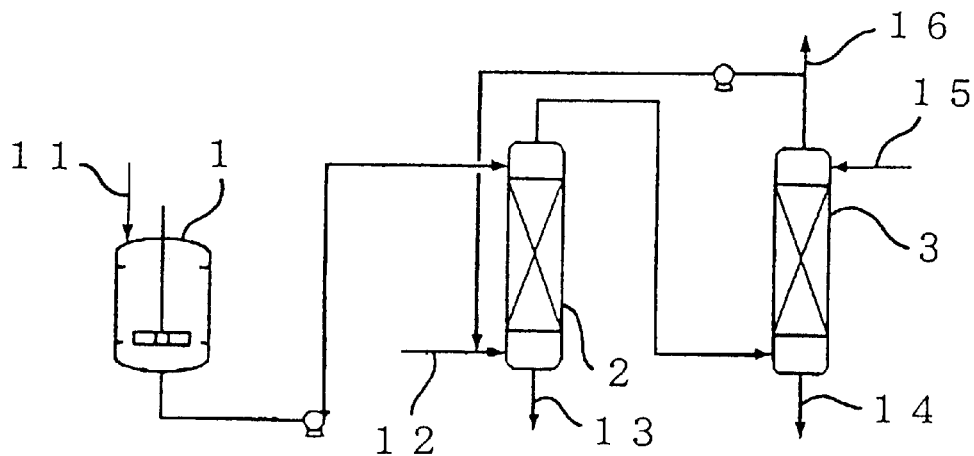
FIG. 2 is a flow chart which illustrates an example of production processes utilizing the production process according to the present invention.
Figure 3:
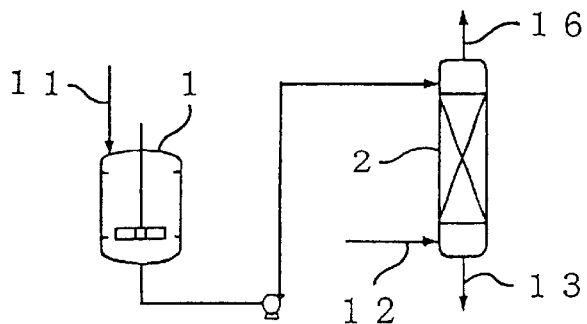
FIG. 3 is a flow chart which illustrates an example of production processes utilizing the production process according to the present invention.
Figure 4:
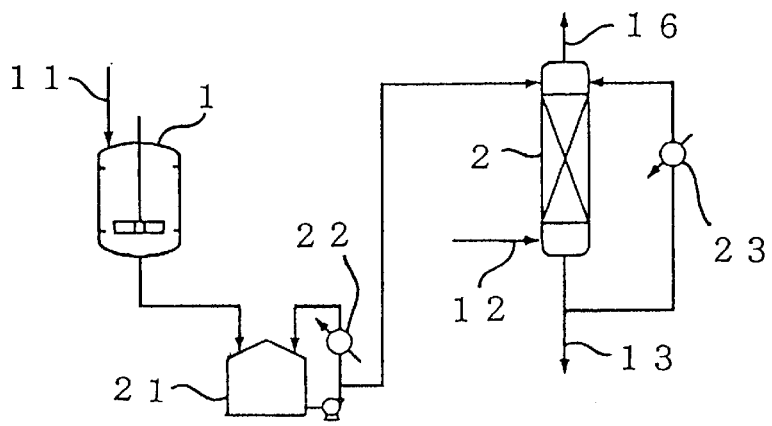
FIG. 4 is a flow chart which illustrates an example of production processes utilizing the production process according to the present invention.
Figure 5:
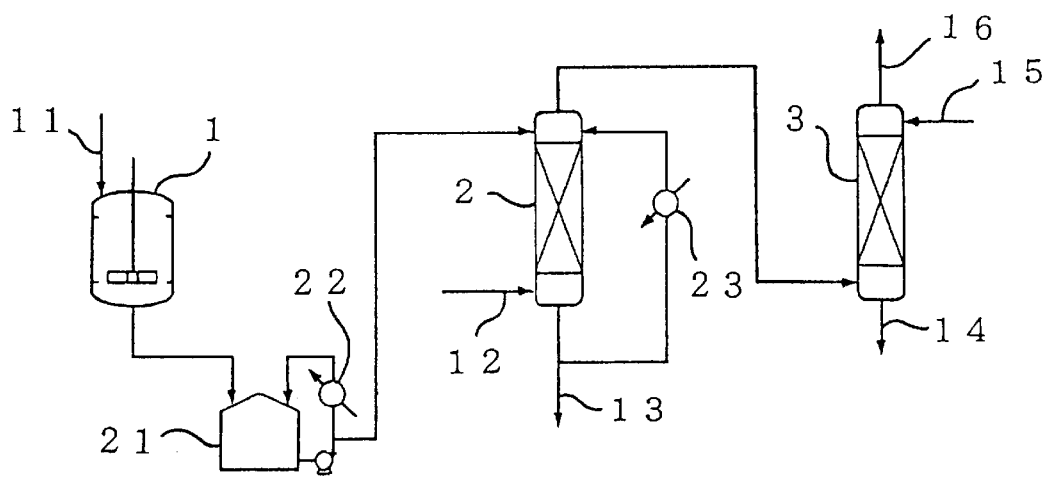
FIG. 5 is a flow chart which illustrates an example of production processes utilizing the production process according to the present invention.

1: Reactor
2: Stripping column
3: Absorption column
4: Absorption column
11: Line for adding raw materials
12: Line for introducing an inert gas
13: Line for extracting a liquid left behind in the stripping step
14: Line for extracting a liquid resultant from the absorption step
15: Line for introducing an absorbing solvent
16: Line for a waste gas
17: Line for a stripped gas
18: Line for re-supplying
21: Intermediate tank
22: Cooler
23: Heater
24: Liquid re-distributor
25: Chimney tray

DETAILED DESCRIPTION OF THE INVENTION

The present invention is explained in detail below.

First, the production process for a hydroxyalkyl(meth) acrylate to which the characteristic production process according to the present invention is preferably applicable is roughly explained as follows.

First, an addition reaction between (meth)acrylic acid and the alkylene oxide is carried out in the presence of a catalyst. The conversion in this addition reaction is often less than 100%, therefore generally such as the unreacted residue of the (meth)acrylic acid or alkylene oxide is present in the resultant reaction liquid at the end of the reaction. Thus, the above reaction liquid is led to the step to remove such as these unreacted residues of raw materials from the reaction liquid, and then purified by such as distillation as the subsequent final step, with the result that the aimed hydroxyalkyl(meth)acrylate is obtained.

When the present invention is carried out, the amount of raw materials as charged for the above reaction between (meth)acrylic acid and the alkylene oxide is such that the alkylene oxide is preferably in the range of 1.0 to 2.0 mols, more preferably in the range of 1.1 to 1.7 mols, still more preferably in the range of 1.2 to 1.5 mols, per 1 mol of (meth)acrylic acid. In the case where the amount of the alkylene oxide as charged is smaller than 1.0 mol, there are disadvantages in that the conversion is lowered to increase the by-products. In addition, in the case where the amount of the alkylene oxide as charged is larger than 2 mols, there are economical disadvantages.

When carrying out the present invention, the mode of the reaction between (meth)acrylic acid and the alkylene oxide is not especially limited, but, for example, any of continuous reaction, batch reaction and semi-batch reaction can be applied.

When carrying out the present invention, the catalyst used for the above reaction between (meth)acrylic acid and the alkylene oxide is not especially limited, but, for example, conventional homogeneous or heterogeneous catalysts for addition reactions can be used. In addition, polymerization inhibitors such as hydroquinone, hydroquinone monomethyl ether and phenothiazine can be added to the reaction liquid, if necessary.

The production process for a hydroxyalkyl(meth)acrylate, according to the present invention, is characterized by a means to remove the unreacted residue of the alkylene oxide from the reaction liquid after the reaction between (meth) acrylic acid and the alkylene oxide in the above series of production processes. The characteristic production process according to the present invention is explained below.

The reaction liquid, resultant from the addition reaction between (meth)acrylic acid and the alkylene oxide, usually contains the unreacted residue of the alkylene oxide together with the hydroxyalkyl(meth)acrylate which is the aimed product. In order to remove this unreacted residue of the alkylene oxide, the reacted liquid is introduced into the stripping step in the below-mentioned way. Then, it is generally preferable, for enhancing the stripping efficiency, that the temperature of the reacted liquid is high when the reacted liquid is introduced into the stripping step. However, re-heating the liquid containing the alkylene oxide involves a danger of explosion and is therefore unfavorable. Thus, the inventors studied to seek a process that can enhance the stripping efficiency even if the reaction liquid is not heated before the stripping step. As a result, the inventors found that: if the reaction liquid resultant from the reaction is directly supplied to the stripping step without being heated, then the stripping efficiency is enhanced due to sensible heat of the reaction liquid, and further, there is no danger of explosion. This is one of the production processes according to the present invention for a hydroxyalkyl(meth)acrylate. Specific examples of the mode of direct supply to the stripping step without heating include a mode in which the reacted liquid is supplied into a stripping apparatus in a state where the temperature of the reacted liquid is kept as far as possible after the reaction, but there is no limitation to this.

In addition, the temperature of the reaction liquid, as is immediately after the reaction, is limited preferably into the range of 40 to 130° C., more preferably 50 to 90° C., for example, also in order to enhance the reaction yield and inhibit the formation of by-products.

The above stripping apparatus is not especially limited, but examples of those which are preferable for the enhancement of the stripping efficiency include packed columns and plate columns such as bubble cap columns and perforated-plate columns.

By vaporization under reduced pressure or by use of an inert gas, the unreacted residue of the alkylene oxide is stripped from the alkylene-oxide-containing reacted liquid as has been supplied into the stripping apparatus, and then the vaporized gas of the alkylene oxide or the alkylene-oxide-containing inert gas, resultant from this stripping, is disposed of or, if necessary, introduced into an absorption apparatus containing an absorbing solvent. Especially, the use of the inert gas is preferable in that the danger of explosion caused by the rise of the temperature due to the adiabatic compression of a gas resultant from vaporization of the alkylene oxide under reduced pressure can be much avoided, with the result that a safe production process can be provided. The main component of the inert gas used for the stripping is not especially limited, but nitrogen gas is preferable in view of cost. However, in the case where only the inert gas such as nitrogen gas is used, the reacted liquid containing the hydroxyalkyl(meth)acrylate which is an easily polymerizable compound might undergo asphyxiation polymerization in the stripping apparatus. Thus, the present inventors diligently studied and, as a result, found that if the concentration of oxygen in the inert gas such as nitrogen gas is adjusted in the specific range of 0.1 to 5 mol %, then the asphyxiation polymerization in the stripping apparatus can be inhibited enough, and further that if the oxygen concentration is in the above range, then there is no danger of explosion. This adjustment of the oxygen concentration can be accomplished, for example, by adding an appropriate amount of air. In addition, it is also preferable to add polymerization inhibitors such as hydroquinone, hydroquinone monomethyl ether and phenothiazine into the reacted liquid in the ratio of 1 weight ppm to 1 weight % of the reacted liquid as another means of inhibiting the asphyxiation polymerization in the stripping apparatus.

In the case where the unreacted residue of (meth)acrylic acid is present in the reacted liquid and where this reacted liquid is supplied to the stripping apparatus in a state where the temperature of the reacted liquid is kept after the reaction, the reacted liquid resides in the stripping apparatus at a comparative high temperature. As a result, a side reaction between this unreacted (meth)acrylic acid and the hydroxyalkyl(meth)acrylate occurs to form an alkylene glycol di(meth)acrylate (hereinafter referred to as diester) as a by-product. Thus, for inhibiting the formation of the by-product, it is preferable that the concentration of the unreacted residue of the (meth)acrylic acid in the reaction liquid which is subjected to the stripping step is suppressed to not higher than 10 weight %.

The vaporized gas of the alkylene oxide or the alkylene-oxide-containing inert gas, as stripped from the stripping apparatus, is then disposed of or, if necessary, supplied to a subsequent absorption apparatus and then absorbed into a solvent in the absorption apparatus. The absorption apparatus is not especially limited, but examples of those which are preferable for the enhancement of the absorption efficiency include packed columns and plate columns such as bubble cap columns and perforated-plate columns. In addition, the alkylene oxide is recovered by being absorbed into a solvent in the above absorption step, therefore this absorption step is more excellent in respect to cost and safety than conventional recovery steps by condensation methods.

In the case where the inert gas is used for the stripping, the inert gas needs to be disposed of outside the system after the stripping step or absorption step. Disposal of the whole inert gas is economically disadvantageous, therefore it is economically advantageous and a preferred mode of the present invention that only a part of the inert gas is disposed of outside the system, and that the greater part of the rest is recycled to the stripping apparatus.

In the mode further comprising the absorption step after the stripping step, the operational pressures in the stripping step and the absorption step are operatable whether the operational pressure in the absorption step is higher or lower than that in the stripping step. However, the lower the operational pressure in the stripping step is, the higher the stripping efficiency is. In addition, the higher the operational pressure in the absorption step is, the higher the absorption efficiency is. Therefore, as the operational pressure in the absorption step is got considerably higher than that in the stripping step, theoretically both the stripping efficiency and the absorption efficiency become better. However, in the case where the operational pressure in the absorption step is got considerably higher than that in the stripping step, the stripped gas containing the alkylene oxide becomes adiabatically compressed with such as a compressor, so there occurs a danger of explosion due to the rise of the temperature. Thus, the present inventors studied about to what extent the difference in operational pressure between the stripping step and the absorption step can be reduced in the case where an attempt is made to maintain both the stripping efficiency and the absorption efficiency on practical use levels. As a result, the present inventors found that if the difference in operational pressure between the stripping step and the absorption step is not more than 1,000 hPa, then the alkylene oxide can safely and efficiently be stripped and absorbed.

In addition, in the case where the inert gas is recycled, it is necessary to raise the pressure in order to return the gas (as discharged from the absorption apparatus) to the stripping apparatus. The present inventors found that also in this case, the alkylene oxide can safely be stripped and absorbed if the difference in operational pressure between the stripping step and the absorption step is suppressed to not more than 1,000 hPa. As is mentioned above, to achieve the object to strip the unreacted alkylene oxide safely and efficiently, the present invention production processes for a hydroxyalkyl(meth)acrylate are characterized by the following four modes respectively in which: (1) the stripping step is performed by use of an inert gas, and the concentration of oxygen in the inert gas is adjusted in the range of 0.1 to 5 mol %; (2) the concentration of the unreacted residue of the (meth)acrylic acid in the resultant reaction liquid is suppressed to not higher than 10 weight %; (3) the difference in operational pressure between the stripping step and the absorption step is suppressed to not more than 1,000 hPa; and (4) the reaction liquid resultant from the reaction is directly supplied to the stripping step without being heated. However, the inventors studied to seek a process that can enhance the stripping efficiency even if the reaction liquid is not heated before the stripping step. As a result, the inventors completed another present invention production process (5) below.

That is to say, another production process (5) for a hydroxyalkyl(meth)acrylate, according to the present invention, comprises the steps of carrying out a reaction between (meth)acrylic acid and an alkylene oxide and stripping the unreacted residue of the alkylene oxide from the resultant reaction liquid, with the production process being characterized in that a part of the liquid left behind in the stripping step is heated and then supplied to the stripping step again.

If a part of the liquid left behind in the stripping step is heated and then supplied to the stripping step again in accordance with this process, the stripping temperature in the stripping step can be raised, so the stripping efficiency can be enhanced. Furthermore, the alkylene oxide content in the liquid left behind in the stripping step is extremely low, so there is no danger of explosion even if this liquid is heated.

In addition, the use of this process enables to raise the stripping temperature in the stripping step by heating and then re-supplying the liquid left behind in the stripping step, and therefore has the advantage of making it unnecessary to beforehand raise the temperature of the reaction liquid, as introduced into the stripping step, to a temperature necessary for the stripping. That is to say, the reaction liquid resultant from the reaction may be supplied directly to the stripping step without being heated, or may be stored in such as an intermediate tank having a cooling apparatus, and then supplied to the stripping step after the temperature of the reaction liquid has fallen. Needless to say, before being introduced into the stripping step, the reaction liquid as once cooled with such as the intermediate tank may be heated to such an extent that there can be no danger of explosion and that the enhancement of the stripping efficiency can be recognized so much that the energy cost of the heating operation can be supplemented. A preferable mode is that the reaction liquid resultant from the reaction is supplied to the stripping step without being heated, and a more preferable mode is that the reaction liquid resultant from the reaction is stored in such as an intermediate tank having a cooling apparatus, and then supplied to the stripping step after the temperature of the reaction liquid has fallen.

In the case where the temperature of the reaction liquid resultant from the reaction is lowered by putting the above intermediate tank between a reactor and the stripping step in the above way, the temperature is lowered preferably to not higher than 40° C., more preferably into the range of 10 to 40° C., still more preferably into the range of 15 to 35° C., particularly preferably into the range of 20 to 30° C.

In addition, heating the liquid left behind in the stripping step is performed so that the temperature can rise preferably into the range of 40 to 80° C., more preferably into the range of 50 to 70° C., still more preferably into the range of 60 to 70° C. In the case where the liquid temperature is lower than 40° C. after heating, the enough enhancement of the stripping efficiency is not seen. In the case where the liquid temperature is higher than 80° C. after heating, there are disadvantages in that there tend to occur problems of explosion or the increase of by-products in the stripping step.

The type of the heater as used for the above heating is not especially limited, but examples thereof include shell-and-tube heat exchangers, spiral heat exchangers, plate heat exchangers and double pipe heat exchangers.

In the case where a part of the liquid left behind in the stripping step is heated and then supplied to the stripping step again, the amount of the liquid as supplied again needs to be such as can supply the heat quantity necessary for the enough enhancement of the stripping efficiency. Such an amount is preferably in the range of 0.1 to 20 times, more preferably 0.3 to 10 times, still more preferably 0.5 to 5 times, as large as the amount of the reaction liquid as supplied to the stripping step.

Examples of flow charts of production processes utilizing the above present invention production processes (1) to (5) for a hydroxyalkyl(meth)acrylate are shown in FIGS. 1 to 5 respectively. Needless to say, the production process utilizing the production process according to the present invention is not limited to these.

In addition, as is mentioned below, to achieve the object to economically and efficiently recover and recycle the unreacted residue of the alkylene oxide, the present invention production processes for a hydroxyalkyl(meth)acrylate are characterized by the following modes (6) to (8) respectively on the premise that the production processes further comprise the absorption step.

The production process (6), one of the production processes according to the present invention, is characterized in that a hydroxyalkyl(meth)acrylate solution is used as the absorbing solvent for the unreacted residue of the alkylene oxide. The hydroxyalkyl(meth)acrylate has more excellent capacity to absorb the alkylene oxide and is therefore more excellent as the absorbing solvent, when compared with (meth)acrylic acid. In addition, the lower the absorption temperature during the absorption is, the better the absorption efficiency is. However, for example, (meth)acrylic acid has so high a solidifying point of about 15° C. that the temperature of absorption by (meth)acrylic acid substantially cannot be set at not higher than 20° C. However, the hydroxyalkyl(meth)acrylate has so low a solidifying point of about −70° C. that the temperature of absorption by the hydroxyalkyl(meth)acrylate can be lowered to not higher than 20° C., or more lowered even to a fairly low temperature. The ratio of the hydroxyalkyl(meth)acrylate to other components in the hydroxyalkyl(meth)acrylate solution which is used as the absorbing solvent in this process is not especially limited, but the higher ratio of the hydroxyalkyl (meth)acrylate is more preferable if lowering the absorption temperature is the only object. In addition, the kind of the component other than the hydroxyalkyl(meth)acrylate in the hydroxyalkyl(meth)acrylate solution which is used as the absorbing solvent in this process is not especially limited, but any of components such as (meth)acrylic acid, water, benzene, toluene and xylene is available.

After absorbing the alkylene oxide, the hydroxyalkyl (meth)acrylate solution which is used as the absorbing solvent in this process may be subjected to addition of (meth)acrylic acid or alkylene oxide fitly if necessary, and then recycled as a raw material for producing the hydroxyalkyl(meth)acrylate. Or the alkylene oxide may be separated from the solvent and then used as a raw material for processes of producing other alkylene oxide derivatives.

Another production process (7) according to the present invention is characterized in that a part of the liquid resultant from the absorption step is cooled and then supplied to the absorption step again.

If alkylene oxide vapor gets absorbed into the solvent, the temperature of the solvent rises due to latent heat of vaporization of the alkylene oxide, therefore the absorption efficiency is deteriorated. Thus, if a part of the liquid resultant from the absorption step is cooled and then supplied to the absorption step again, the temperature of the solvent can be inhibited from rising, so the absorption efficiency can be enhanced.

Figure 6:
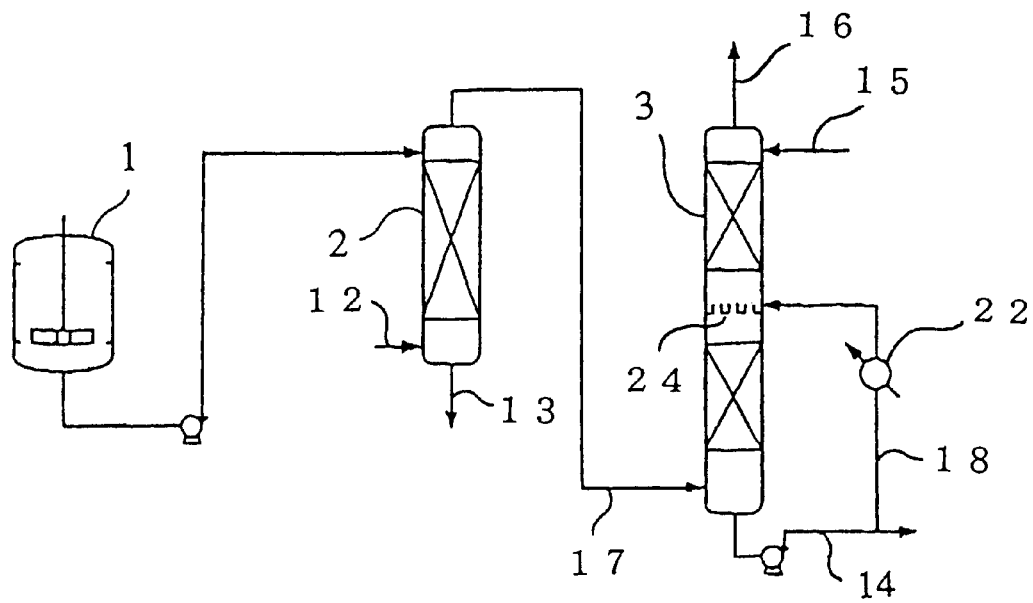
FIG. 6 is a flow chart which illustrates an example of the production process according to the present invention (in this example, only one absorption column is used and a part of the liquid from the absorption column is cooled and then supplied again).
Figure 7:
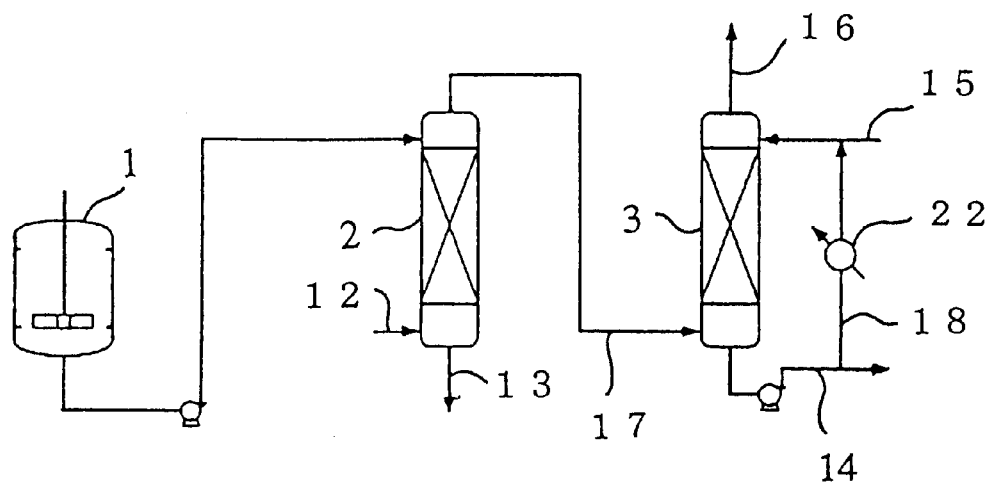
FIG. 7 is a flow chart which illustrates an example of the production process according to the present invention (in this example, only one absorption column is used and a part of the liquid from the absorption column is cooled and then supplied to the column top again).
Figure 8:
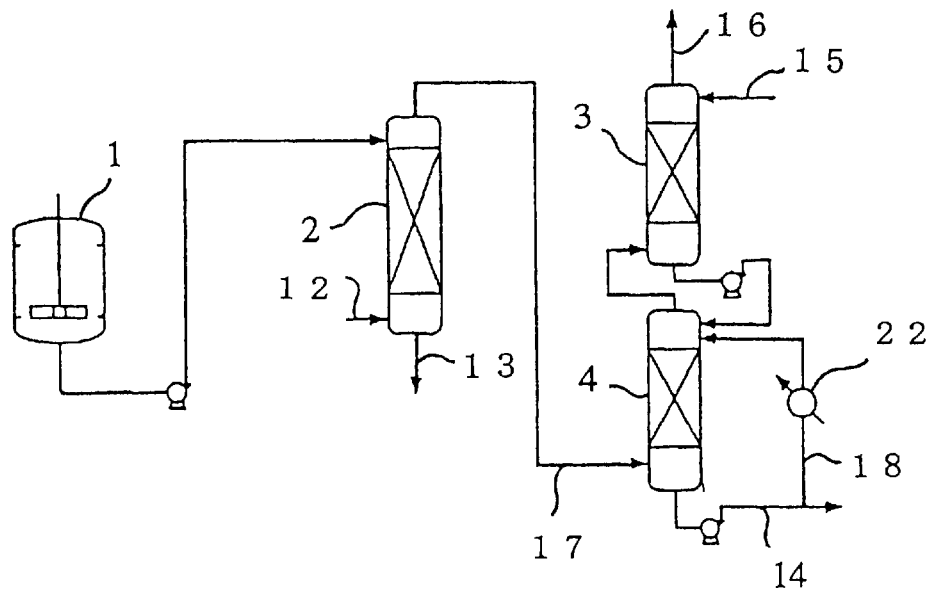
FIG. 8 is a flow chart which illustrates an example of the production process according to the present invention (in this example, two absorption columns are used and a part of the liquid from the bottom absorption column is cooled and then supplied to the bottom absorption column again).

Specifically, in the case where only one absorption column is used in the absorption step, for example, as is illustrated in FIGS. 6 and 7, a part of the liquid from the absorption column bottom (the temperature of this liquid is a risen one due to the absorption of the alkylene oxide) is passed through a cooler to lower the liquid temperature, and then the resultant liquid is supplied into the absorption column again. In addition, in the case where two or more absorption columns are used in the absorption step, for example, as is illustrated in FIG. 8 (case of two absorption columns), a part of the liquid from the bottom absorption column (the temperature of this liquid is a risen one due to the absorption of the alkylene oxide) is passed through a cooler to lower the liquid temperature, and then the resultant liquid is supplied into an absorption column again. In this case, the absorption column into which the liquid is supplied again may be the bottom absorption column as illustrated in FIG. 8, or may be another absorption column.

Examples of the absorbing solvent include the hydroxyalkyl(meth)acrylate solution, (meth)acrylic acid, water, benzene, toluene and xylene. However, the hydroxyalkyl(meth)acrylate is preferable because its capacity to absorb the alkylene oxide is excellent.

As the amount of the liquid resultant from the absorption which is supplied to the absorption column again becomes larger than that of the absorbing solvent (line 15 in FIGS. 6 to 8), the absorption efficiency is enhanced more and more. However, in the case where the amount of the above liquid is too large, there are economical disadvantages in that the pump capacity and the heat quantity for cooling increase so much that vast energy is required. Therefore, actually, the amount of the liquid resultant from the absorption which is supplied to the absorption column again is preferably not larger than 100 times, more preferably not larger than 50 times, particularly preferably not larger than 10 times, of that of the absorbing solvent.

In this production process, when the liquid is re-supplied after being cooled by use of the cooler, the temperature of the liquid is preferably in the range of 0 to 40° C., more preferably in the range of 5 to 30° C., particularly preferably in the range of 10 to 20° C. In the case where the temperature is higher than 40° C., there are disadvantages in that the temperature rise of the absorbing solvent cannot sufficiently be inhibited. In addition, in the case where the temperature is lower than 0° C., there are economical disadvantages in that a vast cost is needed for cooling. In addition, the type of this cooler is not especially limited, but examples thereof include shell-and-tube heat exchangers, spiral heat exchangers, plate heat exchangers and double pipe heat exchangers.

Yet another production process (8) according to the present invention is characterized in that a part or the whole of the absorbing liquid which is on the way of the absorption step is extracted and then cooled and then supplied to the absorption step again.

As is explained above, if alkylene oxide vapor gets absorbed into the solvent, the temperature of the solvent rises due to latent heat of vaporization of the alkylene oxide, therefore the absorption efficiency is deteriorated. Thus, if a part or the whole of the absorbing liquid which is on the way of the absorption step is extracted and then cooled and then supplied to the absorption step again, the temperature of the solvent can be inhibited from rising, so the absorption efficiency can be enhanced.

Figure 9:
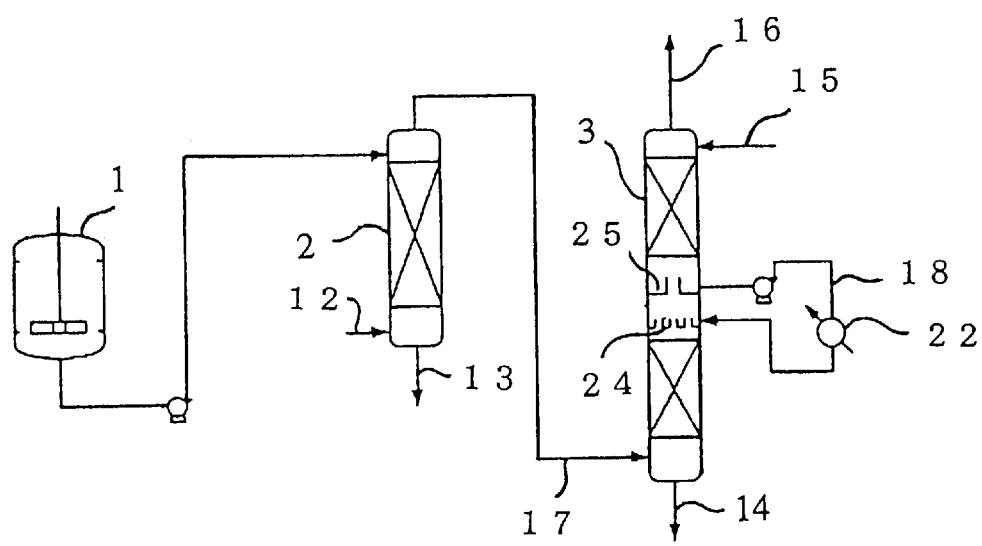
FIG. 9 is a flow chart which illustrates an example of the production process according to the present invention (in this example, only one absorption column is used and a part of the liquid which is on the way of the absorption step is cooled and then supplied again).
Figure 10:
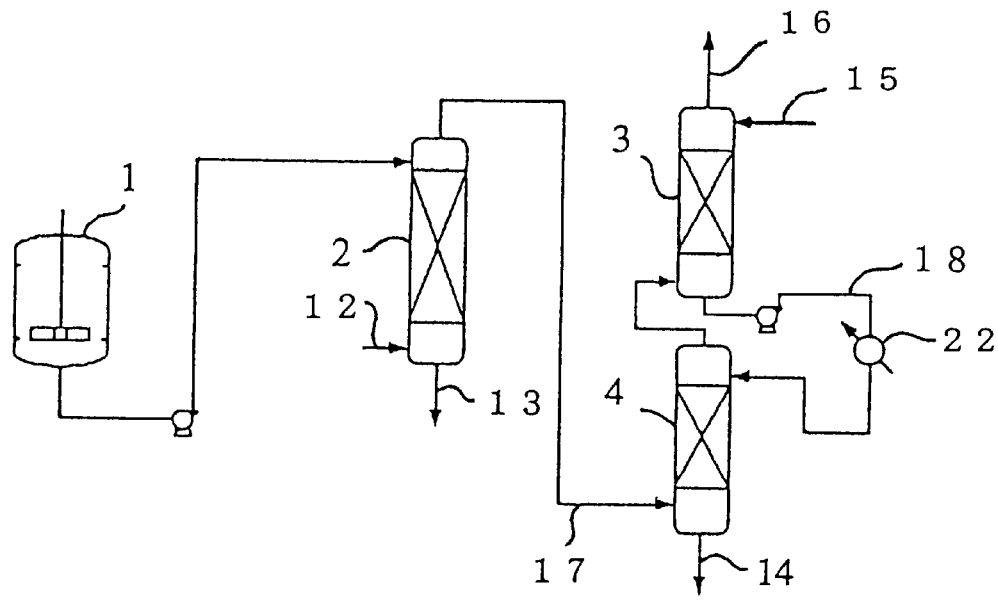
FIG. 10 is a flow chart which illustrates an example of the production process according to the present invention (in this example, two absorption columns are used and a part or the whole of the liquid from the top absorption column is cooled and then supplied to the bottom absorption column again).

Specifically, in the case where only one absorption column is used in the absorption step, for example, as is illustrated in FIG. 9, a part of the absorbing liquid extracted from the midway portion of the absorption column (the temperature of this liquid is a risen one due to the absorption of the alkylene oxide) is passed through a cooler to lower the liquid temperature, and then the resultant liquid is supplied into the absorption column again. In addition, in the case where two or more absorption columns are used in the absorption step, for example, as is illustrated in FIG. 10 (case of two absorption columns), a part or the whole of the absorbing liquid extracted from the bottom of the top absorption column (the temperature of this liquid is a risen one due to the absorption of the alkylene oxide) is passed through a cooler to lower the liquid temperature, and then the resultant liquid is supplied into an absorption column again. In this case, the absorption column from which the absorbing liquid is extracted may be any column, and the absorption column into which the liquid is supplied again may be the bottom absorption column as illustrated in FIG. 10, or may be another absorption column.

Examples of the absorbing solvent include the hydroxyalkyl(meth)acrylate solution, (meth)acrylic acid, water, benzene, toluene and xylene. However, the hydroxyalkyl(meth)acrylate is preferable because its capacity to absorb the alkylene oxide is excellent.

Figure 11:
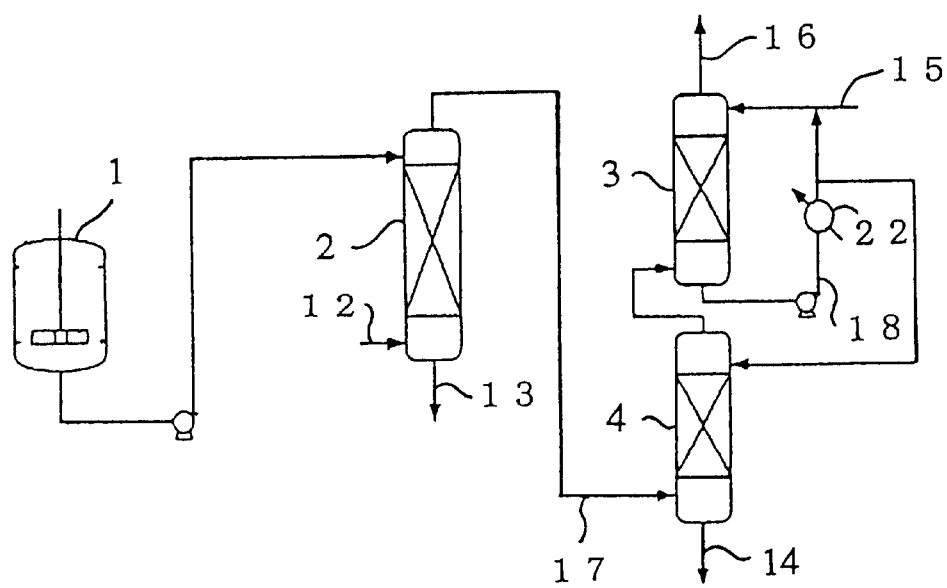
FIG. 11 is a flow chart which illustrates an example of the production process according to the present invention (in this example, two absorption columns are used and a part or the whole of the liquid from the top absorption column is cooled and then supplied to the top absorption column and the bottom absorption column again).

In the case where the liquid extracted from the midway portion of the absorption column is re-supplied to a higher portion than an extraction opening (FIG. 11), as the amount of the re-supplied liquid becomes larger than that of the absorbing solvent which is freshly supplied to the top of the top absorption column (line 15 in FIGS. 9 to 11), the absorption efficiency is enhanced more and more. However, in the case where the amount of the above liquid is too large, there are economical disadvantages in that the pump capacity and the heat quantity for cooling increase so much that vast energy is required. Therefore, actually, the amount of the liquid resultant from the absorption which is supplied to the absorption column again is preferably not larger than 100 times, more preferably not larger than 50 times, particularly preferably not larger than 10 times, of that of the absorbing solvent.

In this production process, when the liquid is re-supplied after being cooled by use of the cooler, the temperature of the liquid is preferably in the range of 0 to 40° C., more preferably in the range of 5 to 30° C., particularly preferably in the range of 10 to 20° C. In the case where the temperature is higher than 40° C., there are disadvantages in that the temperature rise of the absorbing solvent cannot sufficiently be inhibited. In addition, in the case where the temperature is lower than 0° C., there are economical disadvantages in that a vast cost is needed for cooling. In addition, the type of this cooler is not especially limited, but examples thereof include shell-and-tube heat exchangers, spiral heat exchangers, plate heat exchangers and double pipe heat exchangers.

As is mentioned above, the present invention production processes for a hydroxyalkyl(meth)acrylate are characterized by the following modes (1) to (8) respectively. In addition, these production processes (1) to (8) may be used fitly in combinations with each other.

(1) A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that the stripping step is performed by use of an inert gas, and in that the concentration of oxygen in the inert gas is adjusted in the range of 0.1 to 5 mol %.

(2) A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that the concentration of the unreacted residue of the (meth)acrylic acid in the resultant reaction liquid is suppressed to not higher than 10 weight %.

(3) A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that the difference in operational pressure between the stripping step and the absorption step is not more than 1,000 hPa.

(4) A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that the reaction liquid resultant from the reaction is directly supplied to the stripping step without being heated.

(5) A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that a part of the liquid left behind in the stripping step is heated and then supplied to the stripping step again.

(6) A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a hydroxyalkyl(meth)acrylate solution is used as the absorbing solvent.

(7) A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a part of the liquid resultant from the absorption step is cooled and then supplied to the absorption step again.

(8) A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a part or the whole of the absorbing liquid which is on the way of the absorption step is extracted and then cooled and then supplied to the absorption step again.

EFFECTS AND ADVANTAGES OF THE INVENTION

The present invention provides a production process for a hydroxyalkyl(meth)acrylate which comprises the steps of carrying out a reaction between (meth)acrylic acid and an alkylene oxide and stripping the unreacted residue of the alkylene oxide from the resultant reaction liquid, wherein the production process enables to safely and efficiently strip the unreacted residue of the alkylene oxide, or enables to economically and efficiently recover and recycle the unreacted residue of the alkylene oxide.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples of some preferred embodiments.

Hereinafter, the present invention is illustrated by exemplifying the reaction to produce hydroxyethyl acrylate.

EXAMPLE 1

An autoclave as equipped with stirring vanes was charged with 480 ml of an anion-exchange resin (DIAION PA316 produced by Mitsubishi Chemical Corporation) as a catalyst wherein the anion-exchange resin was in a water-swollen state. Then, 229 g/h of ethylene oxide and 288 g/h of acrylic acid (molar ratio of ethylene oxide/acrylic acid=1.3) were continuously supplied into the autoclave to carry out a reaction under conditions where the reaction temperature was 70° C. and where the residence time was 4.1 hours. The pressure during the reaction was about 4,200 hPa. The reacted liquid from the outlet of the autoclave was analyzed, with the result that the content of unreacted acrylic acid, the content of unreacted ethylene oxide, the conversion of acrylic acid, and the conversion of ethylene oxide were 5.6 weight %, 13.4 weight %, 90.0% and 69.8% respectively. As to by-products, the content of diester was 0.22 weight %, and the content of diethylene glycol monoacrylate was 2.2 weight %. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of hydroxyethyl acrylate was supplied as an absorbing liquid from the column top. This absorbing liquid was supplied at 10° C. The liquid from the bottom of the stripping column was analyzed, with the result that the content of ethylene oxide was 1.5 weight %. This corresponds to the unreacted ethylene oxide stripping efficiency of 87.9%. In addition, the increase of diester was not seen. The stripping column top gas was sampled and then given an ignition energy of 300 W in a pressure-resistant container of 2 liters, but no explosion occurred. The absorbing liquid from the column bottom was analyzed, with the result that the content of ethylene oxide was 15.6 weight %. This corresponds to the unreacted ethylene oxide recovery efficiency of 76.7%. In this case, the formation of polymers was not seen either in the stripping column or absorption column. In the above way, a stable operation could safely be performed.

EXAMPLE 2

A reaction to produce hydroxyethyl acrylate was performed in the same way as of Example 1 except that 211 g/h of ethylene oxide and 288 g/h of acrylic acid (molar ratio of ethylene oxide/acrylic acid=1.2) were continuously supplied into the autoclave, and that the reaction temperature was 70° C., and that the residence time was 3.9 hours. The reacted liquid from the outlet of the autoclave was analyzed, with the result that the content of unreacted acrylic acid, the content of unreacted ethylene oxide, the conversion of acrylic acid, and the conversion of ethylene oxide were 11.5 weight %, 13.7 weight %, 80.0% and 67.6% respectively. As to by-products, the content of diester was 0.21 weight %, and the content of diethylene glycol monoacrylate was 2.2 weight %. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. In this case, the liquid from the stripping column was analyzed, with the result that the content of diester was 0.24 weight % which was a little more than that in the reacted liquid, but was within the allowable range as a product.

EXAMPLE 3

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 0.1 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of hydroxyethyl acrylate was supplied as an absorbing liquid from the column top. This absorbing liquid was supplied at 10° C. In this case, the formation of polymers was not seen either in the stripping column or absorption column.

EXAMPLE 4

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of hydroxyethyl acrylate was supplied as an absorbing liquid from the column top. This absorbing liquid was supplied at 20° C. The absorbing liquid from the column bottom was analyzed, with the result that the content of ethylene oxide was 14.2 weight %. This corresponds to the unreacted ethylene oxide recovery efficiency of 69.0%.

EXAMPLE 5

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of hydroxyethyl acrylate was supplied as an absorbing liquid from the column top. This absorbing liquid was supplied at 10° C. In addition, at a rate of 144 g/hr, a part of the absorption column bottom liquid was cooled to 10° C. and then re-supplied to 10 cm below the top of the absorption column. The absorbing liquid from the column bottom was analyzed, with the result that the content of ethylene oxide was 16.8 weight %. This corresponds to the unreacted ethylene oxide recovery efficiency of 84.2%.

EXAMPLE 6

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, a height of 20 cm, and a chimney tray 10 cm below the column top, while 288 g/h of hydroxyethyl acrylate was supplied as an absorbing liquid from the column top. This absorbing liquid was supplied at 10° C. A part of the liquid was extracted from the absorption column through the chimney tray at a rate of 144 g/hr and then cooled to 10° C. and then re-supplied to 10 cm below the top of the absorption column. The absorbing liquid from the column bottom was analyzed, with the result that the content of ethylene oxide was 16.9 weight %. This corresponds to the unreacted ethylene oxide recovery efficiency of 84.4%.

EXAMPLE 7

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of acrylic acid was supplied as an absorbing liquid from the column top. This absorbing liquid was supplied at 20° C. In addition, 144 g/hr of the absorption column bottom liquid was cooled to 20° C. and then re-supplied to 10 cm below the top of the absorption column. The absorbing liquid from the column bottom was analyzed, with the result that the content of ethylene oxide was 14.8 weight %. This corresponds to the unreacted ethylene oxide recovery efficiency of 72.5%.

EXAMPLE 8

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, a height of 20 cm, and a chimney tray 10 cm below the column top, while 288 g/h of acrylic acid was supplied as an absorbing liquid from the column top. This absorbing liquid was supplied at 20° C. A part of the liquid was extracted from the absorption column through the chimney tray at a rate of 144 g/hr and then cooled to 20° C. and then re-supplied to 10 cm below the top of the absorption column. The absorbing liquid from the column bottom was analyzed, with the result that the content of ethylene oxide was 14.9 weight %. This corresponds to the unreacted ethylene oxide recovery efficiency of 72.7%.

EXAMPLE 9

An autoclave as equipped with stirring vanes was charged with 1,152 g of acrylic acid, into which 6.9 g of iron powder was then added and dissolved as a catalyst. The resultant solution was heated to 70° C., and then 776 g of ethylene oxide was added thereto over a period of 2 hours (molar ratio of ethylene oxide/acrylic acid=1.1), and still thereafter the reaction was carried out at 70° C. for two hours. The pressure during the reaction was about 3,920 hPa. The reacted liquid from the outlet of the autoclave was analyzed, with the result that the content of unreacted acrylic acid, the content of unreacted ethylene oxide, the conversion of acrylic acid, and the conversion of ethylene oxide were 0.06 weight %, 0.8 weight %, 99.9% and 98.0% respectively. As to by-products, the content of diester was 0.22 weight %. This reacted liquid was supplied into a stripping column from its top over a period of 4 hours wherein the stripping column had an operational pressure of 5.3 hPa, a column diameter of 40 mm, and a height of 30 cm, while 0.4 g/h of nitrogen gas having an oxygen concentration adjusted to 3 mol % was supplied from the column bottom to carry out the stripping step. The liquid from the bottom of the stripping column was analyzed, with the result that the content of ethylene oxide was 0.04 weight %. This corresponds to the unreacted ethylene oxide stripping efficiency of 95.0%. In addition, the increase of diester was not seen. In this case, the formation of polymers was not seen in the stripping column. In the above way, a stable operation could safely be performed.

EXAMPLE 10

A reaction to produce hydroxyethyl acrylate was performed in the same way as of Example 9, and the reacted liquid was transferred to an intermediate tank. The temperature of the liquid in the intermediate tank was maintained at 20° C. The liquid in this intermediate tank was supplied into a stripping column from its top over a period of 4 hours wherein the stripping column had an operational pressure of 5.3 hPa, a column diameter of 40 mm, and a height of 30 cm, and further, a part of the column bottom liquid was extracted at a rate of 288 g/h from the bottom of the stripping column and then heated to 80° C. and then supplied from the column top, while 0.4 g/h of nitrogen gas having an oxygen concentration adjusted to 3 mol % was supplied from the column bottom to carry out the stripping step. The liquid from the bottom of the stripping column was analyzed, with the result that the content of ethylene oxide was 0.04 weight %. This corresponds to the unreacted ethylene oxide stripping efficiency of 95.0%. In addition, the increase of diester was not seen. In this case, the formation of polymers was not seen in the stripping column. In the above way, a stable operation could safely be performed.

EXAMPLE 11

A reaction to produce hydroxyethyl acrylate was continuously performed in the same way as of Example 1. After being separated from the anion-exchange resin, the reacted liquid was once transferred to an intermediate tank. The temperature of the liquid in the intermediate tank was maintained at 20° C. The liquid in this intermediate tank was continuously supplied into a stripping column from its top wherein the stripping column had an operational pressure of 1,053 hPa, a column diameter of 32 mm, and a height of 30 cm, and further, a part of the column bottom liquid was extracted at a rate of 288 g/h from the bottom of the stripping column and then heated to 80° C. and then supplied from the column top, while 72 g/h of nitrogen gas having an oxygen concentration adjusted to 3 mol % was supplied from the column bottom to carry out the stripping step. The liquid from the bottom of the stripping column was analyzed, with the result that the content of ethylene oxide was 1.5 weight %. This corresponds to the unreacted ethylene oxide stripping efficiency of 87.9%. In addition, the increase of diester was not seen. In this case, the formation of polymers was not seen in the stripping column. In the above way, a stable operation could safely be performed.

Comparative Example 1

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas only was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of hydroxyethyl acrylate was supplied as an absorbing liquid from the column top. This absorbing liquid was supplied at 10° C. In this case, the operation was stopped in about 3 hours, because about 3 g of polymers were formed in the stripping column, which was clogged up with the polymers.

Comparative Example 2

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 10 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of hydroxyethyl acrylate was supplied as an absorbing liquid from the column top. This absorbing liquid was supplied at 10° C. The stripping column top gas was sampled and then given an ignition energy of 300 W in a pressure-resistant container of 2 liters, with the result that there occurred explosion involving a sharp temperature rise.

Comparative Example 3

A reaction to produce hydroxyethyl acrylate was continuously performed in the same way as of Example 1. After being separated from the anion-exchange resin, the reacted liquid was supplied into a stripping column from its top wherein the stripping column had an operational pressure of 27 hPa, a column diameter of 32 mm, and a height of 30 cm, but nitrogen gas was not supplied from the column bottom. The liquid from the bottom of the stripping column was analyzed, with the result that the content of ethylene oxide was 2.9 weight %. This corresponds to the unreacted ethylene oxide stripping efficiency of 76.6%. In addition, in this case, the operation was stopped in about 5 hours, because about 3 g of polymers were formed in the stripping column, which was clogged up with the polymers.

Comparative Example 4

A reaction to produce hydroxyethyl acrylate was continuously performed in the same way as of Example 1. After being separated from the anion-exchange resin, the reacted liquid was supplied into a stripping column from its top wherein the stripping column had an operational pressure of 1,053 hPa, a column diameter of 32 mm, and a height of 30 cm, while 72 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1,013 hPa, a column diameter of 32 mm, and a height of 20 cm, while 288 g/h of acrylic acid was supplied as an absorbing liquid from the column top. This absorbing liquid was supplied at 20° C. The absorbing liquid from the column bottom was analyzed, with the result that the content of ethylene oxide was 13.5 weight %. This corresponds to the unreacted ethylene oxide recovery efficiency of 65.0%.

EXAMPLE 12

The reaction was performed in the same way as of Example 1 except that 220 g/h of ethylene oxide and 288 g/h of acrylic acid (molar ratio of ethylene oxide/acrylic acid= 1.25) were continuously supplied into the autoclave. The reacted liquid from the outlet of the autoclave was analyzed, with the result that the content of unreacted acrylic acid, the content of unreacted ethylene oxide, the conversion of acrylic acid, and the conversion of ethylene oxide were 7.9 weight %, 13.2 weight %, 86.0% and 69.6% respectively. As to by-products, the content of diester was 0.22 weight %, and the content of diethylene glycol monoacrylate was 2.2 weight %.

Next, 50 g of the liquid from the outlet of the autoclave was sampled and then placed into a glass screw tube. After this tube had been immersed in an oil bath of 70° C. for 2 hours, the sampled liquid in this tube was analyzed, with the result that the content of diester was 0.23 weight % which was a little more than that in the reacted liquid, but was within the allowable range.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that the stripping step is performed by use of an inert gas, and in that the concentration of oxygen in the inert gas is adjusted in the range of 0.1 to 5 mol %.

2. A production process according to claim 1, wherein the concentration of the unreacted residue of the (meth)acrylic acid in the resultant reaction liquid is suppressed to not higher than 10 weight %.

3. A production process according to claim 1, wherein the inert gas is used in the stripping step and then recycled to the stripping step.

4. A production process according to claim 2, wherein the inert gas is used in the stripping step and then recycled to the stripping step.

5. A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that the concentration of the unreacted residue of the (meth)acrylic acid in the resultant reaction liquid is suppressed to not higher than 10 weight %.

6. A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that the difference in operational pressure between the stripping step and the absorption step is not more than 1,000 hPa.

7. A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that the reaction liquid resultant from the reaction is directly supplied to the stripping step without being heated.

8. A production process for a hydroxyalkyl(meth)acrylate, which comprises the steps of carrying out a reaction between (meth)acrylic acid and an alkylene oxide and stripping the unreacted residue of the alkylene oxide from the resultant reaction liquid, with the production process being characterized in that a part of the liquid left behind in the stripping step is heated and then supplied to the stripping step again.

9. A production process according to claim 8, wherein the reaction liquid resultant from the reaction is supplied to the stripping step without being heated.

10. A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a hydroxyalkyl(meth)acrylate solution is used as the absorbing solvent.

11. A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a part of the liquid resultant from the absorption step is cooled and then supplied to the absorption step again.

12. A production process for a hydroxyalkyl(meth)acrylate, which comprises the steps of: carrying out a reaction between (meth)acrylic acid and an alkylene oxide; stripping the unreacted residue of the alkylene oxide from the resultant reaction liquid; and causing a solvent to absorb the stripped alkylene oxide; with the production process being characterized in that a part or the whole of the absorbing liquid which is on the way of the absorption step is extracted and then cooled and then supplied to the absorption step again.

* * * * *